US00PP37827P2

(12) United States Plant Patent
Bernuetz

(10) Patent No.: US PP37,827 P2
(45) Date of Patent: Oct. 27, 2026

(54) ***SCAEVOLA* PLANT NAMED 'Bonsca 0205'**

(50) Latin Name: *Scaevola aemula*
Varietal Denomination: BONSCA 0205

(71) Applicant: Andrew Bernuetz, Yellow Rock (AU)

(72) Inventor: Andrew Bernuetz, Yellow Rock (AU)

(73) Assignee: BONZA BOTANICALS PTY. LTD., Yellow Rock (AU)

( * ) Notice: Subject to any disclaimer, the term of this patent is extended or adjusted under 35 U.S.C. 154(b) by 0 days.

(21) Appl. No.: 19/560,028

(22) Filed: Mar. 7, 2026

(51) Int. Cl.
*A01H 6/00* (2018.01)
*A01H 5/02* (2018.01)

(52) U.S. Cl.
USPC ..... Plt./363

(58) Field of Classification Search
USPC ..... Plt./363
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Scaevola* plant named 'Bonsca 0205', characterized by its compact and mounding to outwardly spreading plant habit; moderately vigorous growth habit; freely branching habit; early and freely flowering habit; long flowering period; flowers that are dark purple in color; and good container and garden performance.

2 Drawing Sheets

Figure 1:
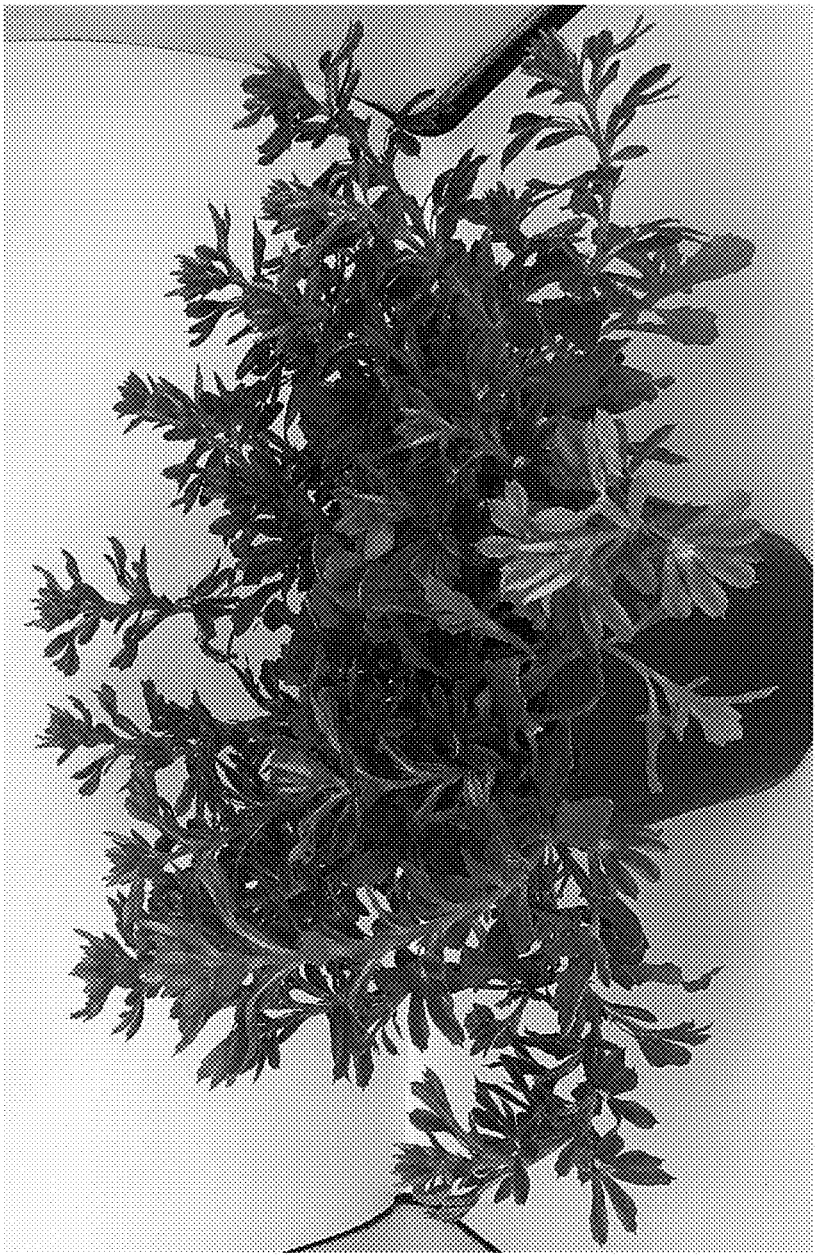

Botanical designation: *Scaevola aemula.*
Cultivar denomination: 'BONSCA 0205'.

BACKGROUND OF THE INVENTION

The present invention relates to a new and distinct cultivar of *Scaevola* plant, botanically known as *Scaevola aemula* and hereinafter referred to by the name 'Bonsca 0205'.

The new *Scaevola* plant a product of a planned breeding program conducted by the Inventor in Yellow Rock, New South Wales, Australia. The objective of the breeding program is to create new compact and mounding *Scaevola* plants with numerous attractive flowers.

The new *Scaevola* plant originated from a cross-pollination conducted by the Inventor in Yellow Rock, New South Wales, Australia in February, 2019 of a proprietary selection of *Scaevola aemula* identified by the code number 16-136, not patented, as the female, or seed, parent with one of five possible unnamed proprietary selections of *Scaevola aemula* (collected as bulk pollen), not patented, as the male, or pollen, parent. The new *Scaevola* plant was discovered and selected by the Inventor as a single flowering plant from within the progeny of the stated cross-pollination in a controlled greenhouse environment in Yellow Rock, New South Wales, Australia in January, 2020.

Asexual reproduction of the new *Scaevola* plant by vegetative tip cuttings in a controlled greenhouse environment in Yellow Rock, New South Wales, Australia since January, 2020 has shown that the unique features of this new *Scaevola* plant are stable and reproduced true to type in successive generations.

SUMMARY OF THE INVENTION

Plants of the new *Scaevola* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Bonsca 0205'. These characteristics in combination distinguish 'Bonsca 0205' as a new and distinct *Scaevola* plant:

1. Compact and mounding to outwardly spreading plant habit.
2. Moderately vigorous growth habit.
3. Freely branching habit.
4. Early and freely flowering habit.
5. Long flowering period.
6. Flowers that are dark purple in color.
7. Good container and garden performance.

Plants of the new *Scaevola* can be compared to plants of the female parent selection. Plants of the new *Scaevola* differ primarily from plants of the female parent selection in flower color as plants of the new *Scaevola* have dark purple-colored flower whereas plants of the female parent selection have dark violet-colored flowers.

Plants of the new *Scaevola* can be compared to plants of the male parent selections. Plants of the new *Scaevola* differ primarily from plants of the male parent selections in flower color as plants of the new *Scaevola* have dark purple-colored flowers whereas plants of the male parent selections have dark violet-colored flowers.

Plants of the new *Scaevola* can be compared to plants of the *Scaevola aemula* 'Bonsc 16100', disclosed in U.S. Plant Pat. No. 34,840. In side-by-side comparisons, plants of the new *Scaevola* differ from plants of the 'Bonsc 16100' in the following characteristics:

1. Plants of the new *Scaevola* are more compact than plants of 'Bonsc 16100'.
2. Plants of the new *Scaevola* are not as vigorous as plants of 'Bonsc 16100'.
3. Leaves of plants of the new *Scaevola* are lighter green in color than leaves of plants of 'Bonsc 16100'.

4. Plants of the new *Scaevola* and 'Bonsc 16100' differ in flower color as flowers of plants of the new *Scaevola* are dark purple whereas flowers of plants of 'Bonsc 16100' are deep reddish purple in color.

BRIEF DESCRIPTION OF THE PHOTOGRAPHS

The accompanying colored photographs illustrate the overall appearance of the new *Scaevola* plant showing the colors as true as it is reasonably possible to obtain in colored reproductions of this type. Colors in the photographs may differ slightly from the color values cited in the detailed botanical description which accurately describe the colors of the new *Scaevola* plant.

The photograph on the first sheet (FIG. 1) is a side perspective view of a typical flowering plant of 'Bonsca 0205' grown in a container.

Figure 2:
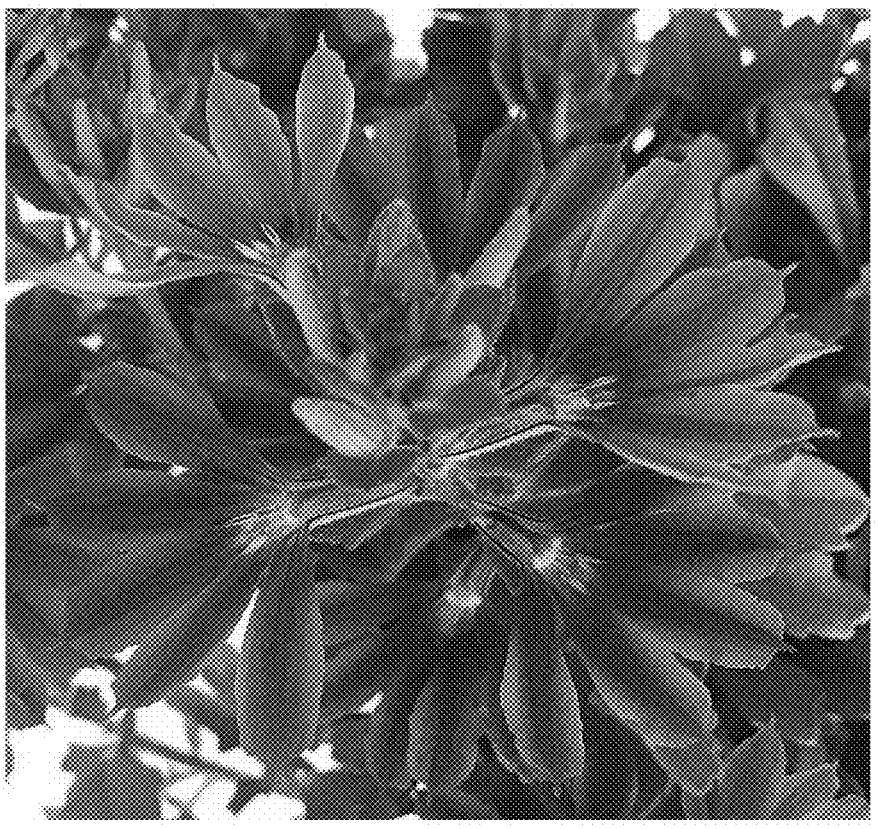

The photograph on the second sheet (FIG. 2) is a close-up view of a typical flowering plant of 'Bonsca 0205'.

DETAILED BOTANICAL DESCRIPTION

The aforementioned photographs and following observations, measurements and values describe plants grown during the spring in 24-cm containers in an outdoor nursery in Higashiomi, Shiga, Japan and under cultural practices typical of commercial *Scaevola* production. During the production of the plants, day temperatures ranged from 15° C. to 30° C. and night temperatures ranged from 13° C. to 25° C. Plants were three months old when the photographs and the detailed description were taken. In the following description, color references are made to The Royal Horticultural Society Colour Chart, 2015 Edition, except where general terms of ordinary dictionary significance are used.

Botanical classification: *Scaevola aemula* 'Bonsca 0205'.

Parentage:

*Female, or seed, parent*.—Proprietary selection of *Scaevola aemula* identified as code number 16-136, not patented.

*Male or pollen parent*.—One of five possible unnamed proprietary selections of *Scaevola aemula* (collected as bulk pollen), not patented.

Propagation:

*Type*.—By vegetative tip cuttings.

*Time to initiate roots, summer*.—About ten days at temperatures about 21° C. to 25° C.

*Time to initiate roots, winter*.—About 15 days at temperatures about 18° C. to 21° C.

*Time to develop roots, summer*.—About three weeks at temperatures about 21° C. to 25° C.

*Time to develop roots, winter*.—About four weeks at temperatures about 18° C. to 21° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact and mounding to outwardly spreading plant habit; moderately vigorous growth habit.

*Branching habit*.—Freely branching habit with lateral branches potentially forming at every node; pinching enhances branching potential.

*Plant height*.—About 15.6 cm.

*Plant diameter* (*area of spread*).—About 37.6 cm.

Lateral branch description:

*Length*.—About 11.6 cm.

*Diameter*.—About 2.1 mm.

*Internode length*.—About 1.8 cm.

*Aspect*.—Upright to outwardly.

*Texture*.—Moderately pubescent; rough.

*Color*.—Close to 138B.

Leaf description:

*Arrangement*.—Alternate, simple; sessile.

*Length*.—About 4.5 cm.

*Width*.—About 1.9 cm.

*Shape*.—Spatulate.

*Apex*.—Obtuse.

*Base*.—Attenuate.

*Margin*.—Moderately serrate.

*Texture, upper and lower surfaces*.—Sparsely pubescent; rough.

*Venation pattern*.—Pinnate, reticulate.

*Color*.—Developing and fully expanded leaves, upper surface: Close to 138A; venation, close to 138B. Developing and fully expanded leaves, lower surface: Close to 138B; venation, close to 138B.

Flower description:

*Flower type and shape*.—Zygomorphic, semi-circular, fan-shaped flowers with five petals fused at the base to form a tubular flower throat; flower throat open along the upper surface exposing the reproductive organs.

*Flower arrangement and quantity*.—Solitary sessile flowers arising from upper leaf axils; flowers mostly horizontal; freely flowering habit with typically about nine flowers per lateral branch and about 171 open flowers per plant at one time.

*Flowering time*.—Early flowering habit, plants begin flowering after about three to four weeks after planting; long flower period, plants flower continuously from spring into autumn in Japan.

*Flower longevity*.—Depending on temperature, individual flowers typically last about a week on the plant; flowers not persistent.

*Fragrance*.—None detected.

*Flower buds*.—Length: About 2.1 cm. Diameter: About 2.5 mm. Shape: Lenticular. Color: Close to 84A.

*Flowers*.—Diameter: About 2 cm by 3.3 cm. Depth: About 1.3 cm. Throat diameter: About 3.7 mm. Tube length: About 1.3 cm. Tube diameter, mid-section: About 2.9 mm. Tube diameter, proximally: About 2.5 mm.

*Petals*.—Quantity per flower: Five, fused at base. Length, beyond tube: About 1.6 cm. Width, beyond tube: About 6.6 mm. Shape: Oblanceolate. Apex: Mucronate. Margin: Entire; slightly undulate. Texture, upper and lower surfaces: Smooth, glabrous. Texture, throat: Pubescent. Texture, tube: Pubescent. Color: When opening and fully opened, upper surface: Close to N81A; venation, close to N81A. When opening and fully opened, lower surface: Close to N81B; midrib, close to 83D, and lateral venation, close to N81B. Throat: Close to N144B; proximally, close to 150B with venation, close to 83A. Tube: Close to 145C; venation, close to N77C.

*Sepals*.—Quantity per flower: Two, opposite. Length: About 4.8 mm. Width: About 1.5 mm. Shape: Linear. Apex: Acute. Base: Fused. Margin: Entire. Texture, upper and lower surfaces: Pubescent; rough. Color, upper and lower surfaces: Close to 138A.

*Reproductive organs*.—Androecium: Stamen quantity per flower: Five. Filament length: About 3.5 mm. Filament color: Close to 150D. Anther size: About 0.5 mm by 1 mm. Anther shape: Ellipsoidal. Anther color: Close to 150D. Pollen: Sparse. Pollen color: Close to 150D. Gynoecium: Pistil quantity per flower: One. Pistil length: About 1.4 cm. Style color: Close to 145B variably tinged with close to N77B. Stigma color: Close to 150D. Ovary color: Close to 145A.

*Seeds and fruits*.—To date, seed and fruit development have not been observed on plants of the new *Scaevola*.

Garden performance: Plants of the new *Scaevola* have been observed to have good garden performance and to tolerate rain, wind and temperatures ranging from about 1° C. to about 40° C.

Pathogen & pest resistance: To date, plants of the new *Scaevola* have not been shown to be resistant to pathogens and pests common to *Scaevola* plants.

It is claimed:

1. A new and distinct *Scaevola* plant named 'Bonsca 0205' as herein illustrated and described.

* * * * *